United States Patent [19]

Hayashi et al.

[11] Patent Number: 4,606,911
[45] Date of Patent: Aug. 19, 1986

[54] PHARMACEUTICAL COMPOSITION FOR THE PREVENTION OF DENTAL CARIES

[75] Inventors: Shin'ichi Hayashi, Osaka; Akiyoshi Yoshida, Nara; Shigeru Kametaka; Tetsuo Koike, both of Osaka, all of Japan

[73] Assignee: Rohto Pharmaceutical Co. Ltd., Osaka, Japan

[21] Appl. No.: 754,300

[22] Filed: Jul. 15, 1985

[30] Foreign Application Priority Data

Jul. 27, 1984 [JP] Japan ................... 59-158164

[51] Int. Cl.⁴ .............. A61K 7/16; A61K 31/215; A61K 31/19
[52] U.S. Cl. ......................... 424/49; 514/529; 514/557; 514/835
[58] Field of Search ............ 514/529, 557, 835; 424/49

[56] References Cited

U.S. PATENT DOCUMENTS 3,328,246  6/1967  Gottfried et al. ............ 424/21
4,022,881  5/1977  Hawking .................... 424/49
4,173,648  11/1979 Pifferi et al. ................. 514/557

FOREIGN PATENT DOCUMENTS 923414   4/1963  United Kingdom ........... 514/557
1229562  4/1971  United Kingdom ........... 514/557
2092442  8/1982  United Kingdom ........... 514/529

OTHER PUBLICATIONS

J. of Med. Chemistry 17(2), 191–194, (1974)–Pitzele.

Primary Examiner—Douglas W. Robinson
Attorney, Agent, or Firm—Robbins & Laramie

[57] ABSTRACT

A pharmaceutical composition for the prevention of dental caries which comprises as essential component(s) one or more of pentacyclic acid triterpenes of the formula:

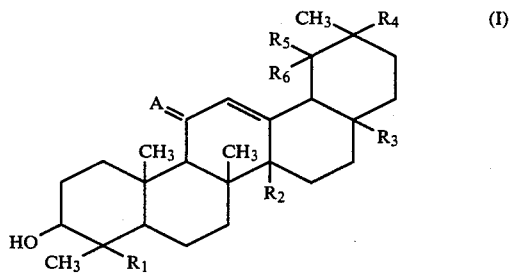

wherein $R_1$ represents $CH_3$, CHO or $CH_2OH$, $R_2$ and $R_3$ independently represent $CH_3$ or COOH, $R_4$ represents H, $CH_3$, COOH or $COOCH_3$, $R_5$ and $R_6$ independently represent H, $CH_3$ or OH, and A represents two Hs or O, and their salts.

8 Claims, No Drawings

PHARMACEUTICAL COMPOSITION FOR THE PREVENTION OF DENTAL CARIES

This invention relates to a pharmaceutical composition useful for the prevention of dental caries. More particularly, it relates to a pharmaceutical composition to be applied to an oral cavity for the purpose of preventing dental caries, which composition comprises as an essential component one or more of pentacyclic acid triterpenes having a selective antibacterial activity to *Streptococcus mutans* present in the oral cavity and/or an activity inhibiting said bacteria and other microorganisms from adhering to the surface of teeth (hereinater, this activity is simply referred to as "adherence-inhibiting activity").

For many years, opinion has been divided about growth and progress of dental caries. However, a theory based on bacterial infection is predominantly accepted in recent years. According to the theory, dental caries occurs by the mechanism as mentioned below.

One of oral microorganisms, *Streptococcus mutans,* produces and excretes an exoenzyme called glucosyltransferase (GTase), which in turn converts sucrose contained in various food to a viscous polysaccharide, i.e., glucan. The polysaccharide adheres, accompanied by oral microorganisms, to the surface of teeth, which results in the formation of a dental plaque. Various microorganisms grow and propagate in the plaque and produce organic acids such as lactic acid through the glycolytic path way. Increase of an acidity of oral fluid up to pH 5.4 or below due to such organic acids causes demineralization of an enamel of teeth, which leads to the occurance and progress of dental caries.

As will be understood from the mechanism as mentioned above, (a) components of food, particularly sucrose: (b) tooth substance susceptible to an attack of organic acids: and (c) oral microorganisms, especially *Streptococcus mutans,* are involved in the dental caries. Accordingly, (1) avoiding the sucrose intake, (2) strengthening the tooth substance, (3) preventing the microorganisms from adhering to teeth surface, and (4) killing *S. mutans* appear to be effective for the prevention of dental caries. However, in the first countermeasure, it is practically impossible to remove all of sucrose from foodstuffs. In the second countermeasure, incorporation of fluorides into tooth paste or tap water for the purpose of strengthening tooth substance is not so efficient as expected, while it has a trend to cause "mottled tooth". Incorporation of a certain enzyme into tooth paste, as the third countermeasure, with the aim of destroying dental plaque is not so effective either.

As the last countermeasure, various germicides and antibiotics have long been employed in an attempt of preventing dental caries by killing microorganisms, particularly *S. mutans,* in oral cavity. However, these disinfectants and antibiotics indiscriminately kill all of the indigenous oral microorganisms, which brings about the change of oral and intestinal flora. Such change, in turn, causes stomatitis, aphtha and paradental diseases because pathogenic bacteria, of which propagation has been suppressed by the indigenous microorganisms, start to grow.

Because of the reason metioned above, disinfectants and antibiotics which kill all of the indigenous oral microorganisms are not desirable for the purpose of preventing dental caries.

As the result of an extensive study seeking a new compound having a selective antibacterial activity to *S. mutans* and/or an adherence-inhibiting activity, it has now been found that pentacyclic acid triterpenes of the formula:

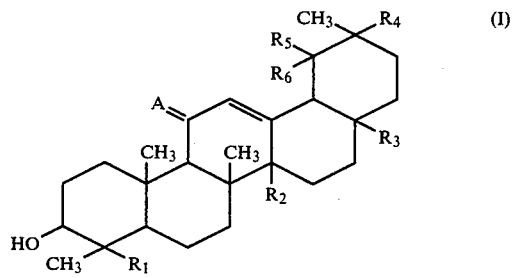

wherein $R_1$ represents $CH_3$, CHO or $CH_2OH$, $R_2$ and $R_3$ independently represent $CH_3$ or COOH, $R_4$ represents H, $CH_3$, COOH or $COOCH_3$, $R_5$ and $R_6$ independently represent H, $CH_3$ or OH, and A represents two Hs or O, and their salts are suitable for this purpose.

Accordingly, this invention provides for a pharmaceutical composition to be applied to an oral cavity for the purpose of preventing dental caries, which comprises as an essential component one or more of pentacyclic acid triterpenes of the formula (I) having a selective antibacterial activity to *S. mutans* and/or an adherence-inhibiting activity.

The invention also provides for a method of preventing dental caries which comprises applying to an oral cavity one or more of the compounds of the formula (I) and pharmaceutically acceptable salts thereof.

The representative pentacyclic acid triterpenes of the formula (I) include oleanolic acid, ursolic acid, pomolic acid, quinovic acid, gypsogenin, hedragenin, phytolaccinic acid and glycyrrhetic acid. These triterpenes are known and naturally occuring compounds. Each of these compounds has a structural formula represented by the formula (I) wherein repective symbols have the meanings shown in Table 1 below.

TABLE 1

| Triterpenes | $R_1$ | $R_2$ | $R_3$ | $R_4$ | $R_5$ | $R_6$ | A |
|---|---|---|---|---|---|---|---|
| Oleanolic A. | $CH_3$ | $CH_3$ | COOH | $CH_3$ | H | H | $H_2$ |
| Ursolic A. | $CH_3$ | $CH_3$ | COOH | H | $CH_3$ | H | $H_2$ |
| Pomolic A. | $CH_3$ | $CH_3$ | COOH | H | $CH_3$ | OH | $H_2$ |
| Quinovic A. | $CH_3$ | COOH | COOH | H | $CH_3$ | H | $H_2$ |
| Hederagenin | $CH_2OH$ | $CH_3$ | COOH | $CH_3$ | H | H | $H_2$ |
| Spergulagenic A. | $CH_3$ | $CH_3$ | COOH | $COOCH_3$ | H | H | $H_2$ |
| Gypsogenin | CHO | $CH_3$ | COOH | $CH_3$ | H | H | $H_2$ |
| Phytolaccinic A. | $CH_2OH$ | $CH_3$ | COOH | $COOCH_3$ | H | H | $H_2$ |
| Glycyrrhetic A. | $CH_3$ | $CH_3$ | $CH_3$ | COOH | H | H | O |

The pentacyclic acid triterpenes of the formula (I) include those which only have an antibacterial activity to *S. mutans,* those which have a weak antibacterial activity and a strong adherence-inhibiting activity, and those which have both of these activities. For instance, oleanolic acid, ursolic acid, pomolic acid and hederagenin have both activities. It should be noted that oleanolic acid and ursolic acid show the adherence-inhibiting action at such low concentration as 10 μg/ml. On the other hand, glycyrrhetic acid has a very strong and selective antibacterial activity to *S. mutans*. The minimum inhibitory concentration (MIC) of this compound to *S. mutans* is lower than 10 μg/ml.

Determination of Antibacterial Activity

Antibacterial activities possessed by oleanolic acid, ursolic acid and glycyrrhetic acid on various types of bacteria were determined according to the method described below.

To a test tube was charged 3.8 ml of Brain Heart Infusion (BHI) medium, and 100 μl of a sample solution containing oleanolic, ursolic or glycyrrhetic acid and 100 μl of pre-incubated culture of bacterium selected from those listed below were added thereto. The mixture was incubated at 37° C. and then allowed to stand over night. The extent of the growth of bacterium was observed after two or five days. The MIC value was determined for each sample and summarized in Table 2.

| Bacteria employed in the test | |
|---|---|
| *Streptococcus mutans* OMZ 176 | (Gram positive) |
| *Streptococcus salivarius* ATCC 9222 | (Gram positive) |
| *Bacillus megaterium* QM B1551 | (Gram positive) |
| *Staphylococcus aureus* 209P | (Gram positive) |
| *Esherichia coli* K12 | (Gram negative) |
| *Serratia marcescens* IFO 12648 | (Gram negative) |
| *Pseudomonas aeruginosa* KM338 | (Gram negative) | ursolic acid also exhibit the selective activity on *S. mutans*, although the magnitude of the activity is each less than that of glycyrrthetic acid. Pomolic acid and hederagenin show almost the same antibacterial activity as oleanolic acid.

As described above, an agent to be used for the prevention of dental caries desirably has both of the selective antibacterial activity to *S. mutans* and the adherence-inhibiting activity. Some of the compounds represented by the formula (I), for example, oleanolic acid, ursolic acid, pomolic acid and hederagenin have both of the adherence-inhibiting activity and the selective antibacterial activity to *S. mutans*. Such adherence-inhibiting activity of these triterpenes was determined according to the method described below.

Method for the Determination of Adherence-Inhibiting Activity

The adherence-inhibiting activity of the triterpenes of the formula (I) was measured using an inner wall of a test tube in place of the surface of a tooth.

To 2.9 ml of BHI medium containing 5% sucrose in a test tube (i) are added 30 μl of a sample solution prepared by dissolving a compound of: the formula (I) in H₂O or dimethylsulfoxide (DMSO) and 100 μl of culture medium containing *S. mutans* OMZ 176 (serotype d) which was preincuvated at 37° C. for 24 hours in BHI medium, and the mixture is incubated at 37° C. for 20 hours, with the test tube being maintained at a slant of 30°. The test tube is revolved gently two or three times and the supernatant is transferred to another test tube (ii). To the first test tube (i) is added 3 ml of 50 mM phosphate buffer (pH 7.5), and the test tube is gently revolved two or three times. The resultant supernatant is transferred to the third test tube (iii). The test tubes

TABLE 2

| Micro- organisms | Antibacterial Activity | | | | | | | | | | | | | | | | | | | | |
|---|---|---|---|---|---|---|---|---|---|---|---|---|---|---|---|---|---|---|---|---|---|
| | Glycyrrhetic acid (μg/ml) | | | | | | | Oleanolic acid (μg/ml) | | | | | | | Ursolic acid (μg/ml) | | | | | | |
| | 10 | 25 | 50 | 100 | 200 | 400 | MIC | 10 | 25 | 50 | 100 | 200 | 400 | MIC | 10 | 25 | 50 | 100 | 200 | 400 | MIC |
| *Streptococcus mutans* OMZ 176 | + | + | + | + | + | + | 10 | − | − | ± | ± | ± | ± | 400 | − | − | + | + | + | + | 25 |
| *Streptococcus salivarius* | − | − | − | − | − | ± | >400 | − | − | − | − | ± | + | 400 | − | − | + | + | + | + | 25 |
| *Bacillus megaterium* | − | + | + | + | + | + | 25 | − | − | − | − | − | − | >400 | − | − | − | − | − | − | >200 |
| *Staphylococcus aureus* | − | − | − | − | − | − | 400 | − | − | − | − | − | − | >400 | | | | | | | |
| *Esherichia coli* | − | − | − | − | − | − | >400 | − | − | − | − | − | − | >400 | | | | | | | |
| *Serratia marcescens* | − | − | − | − | − | − | >400 | − | − | − | − | − | − | >400 | | | | | | | |
| *Pseudomonas aeruginosa* | − | − | − | − | − | − | >400 | − | − | − | − | − | − | >400 | | | | | | | |

− ... grow
± ... slightly grow
+ ... not grow
MIC ... minimum inhibitory concentration Table 2 clearly shows that glycyrrhetic acid exhibits a selective antibacterial activity on *S. mutans* and *Bacillus megaterium*. In other words, *Streptococcus salivarius*, *Staphylococcus aureus*, *Escherichia coli*, *Serratia marcescens*, and *Pseudomonas aeruginosa* remain unaffected by the action of this compound. Thus, glycyrrhetic acid appears the most desirable agent for the protection of dental caries because it exerts its antibacterial action only on undesirable *S. mutans* among various indigenous microorganisms in oral cavity. Oleanolic acid and (ii) and (iii) are each centrifuged and respective supernatants are discarded. To each of the test tubes (i), (ii) and (iii) is added 3 ml of 0.5M NaOH, and the test tubes are shaken to suspend bacterial cells. Absorbance of the resulting suspension is measured at 660 nm. The absorbances obtained with respect to the test tube (i), (ii) and (iii) are represented by Ab(i), Ab(ii) and Ab(iii), respectively. Ab(i) reflects the amount of the bacterial cells adhered to the wall of the test tube and Ab(ii) and Ab(iii) correspond to the amount of the bacterial cells not adhered to the wall.

The same procedure is repeated using 30 µl of distilled water or DMSO in place of the sample solution to obtain a control. The absorbance of the control is represented by Ab(Cont.).

Adherence percentage of bacteria is calculated from the following equation.

$$\text{Adherence (\%)} = \frac{Ab(i)}{Ab(i) + Ab(ii) + Ab(iii)} \times 100$$

Adherence inhibitory percentage (AIP) is calculated using the adherence percentage according to the following equation.

$$AIP = \frac{1 - (\text{Average adherence (\%) of Sample})}{\text{Average adherence (\%) of Control}} \times 100$$

The magnitude of adherence-inhibiting activity of each of the samples is shown, in Table 3, by the use of the following symbols:

| | |
|---|---|
| ++ | inhibition of adherence and growth (AIP > 50%) |
| + | inhibition of adherence (AIP > 50%) |
| ± | week inhibition of adherence (25% < AIP < 50%) |
| − | the same as control (AIP < 25%) |

It should be noted that Table 3 contains the data in connection with various analogous compounds corresponding to the compounds of the formula (I) but not fallen within the scope of the formula (I). The chemical structure of each of the analogous compounds is shown in Table 4.

TABLE 3

| | Adherence-inhibiting activity | | | | | |
|---|---|---|---|---|---|---|
| | Concentration (µg/ml) | | | | | |
| Sample | 100 | 50 | 30 | 20 | 10 | 0 |
| Oleanolic acid | ++ | ++ | ++ | + | + | − |
| Methyl oleanolate (17-position) (a) | − | − | − | − | − | − |
| Oleanolic acid (acid reductant) (b) | − | − | − | − | − | − |
| Oleanolic acid (acetylate of OH at 3-position) (c) | ± | ± | − | − | − | − |
| Oleanolic acid (glucose-glycolate at 3-position) (d) | ± | ± | − | − | − | − |
| Ursolic acid | ++ | ++ | ++ | + | + | − |
| Glycyrrizic acid | − | − | − | − | − | − |
| Chikusetsusaponin V (e) | − | − | − | − | − | − |
| Taraxerol | − | − | − | − | − | − |
| Pfaffic acid | − | − | − | − | − | − |
| Pfaffoside E | − | − | − | − | − | − |
| Pomolic acid | ++ | ++ | ++ | + | − | − |
| Hederagenin | ++ | ++ | ++ | + | − | − |

TABLE 4

Chemical Structure of Analogous Compounds

| Compds. | R7 | R8 |
|---|---|---|
| (a) | OH | COOCH3 |
| (b) | OH | CH2OH |
| (c) | OCOCH3 | COOH |
| (d) | O—Glc | COOH |

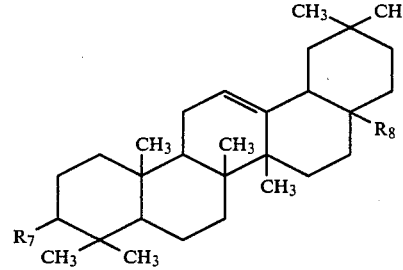

(II)

| | | |
|---|---|---|
| (e) | O—Glc<br>\|<br>Glc.A | COOGlc |

(f)

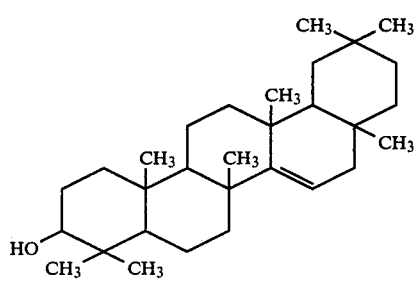

A: H2
Glc: glucose
Glc.A: glucuronic acid

Oleanolic acid, ursolic acid, pomolic acid and hederagenic acid can inhibit the adherence of the bacterial cells at the concentration of 10 µg/ml, which is ineffective for exhibiting antibacterial activity. It was confirmed that these triterpenes completely inhibited the adherence of bacterial cells to the surface of an extracted tooth which was suspended, by means of a wire, in a culture medium containing sucrose.

On the other hand, such antibacterial activity and adherence-inhibiting activity could not be observed in the analogous compounds, such as those wherein the hydroxy group at C-3 of oleanolic acid has been acetylated or glycosylated, those wherein the hydroxy group at C-3 of glycyrrhetic acid has been glycosylated (glycyrrhizic acid), those wherein the carboxylic acid at C-17 of oleanolic acid has been methylated or reduced to an alcohol, those wherein the hydroxy groups at C-3 and C-17 of oleanolic acid have been glycosylated (chikusetsusaponin V), and those corresponding to oleanolic acid but having no carboxylic acid (taraxerole).

It can be concluded, from the results obtained above, that the exertion of an antibacterial activity and an adherence-inhibiting activity in these triterpernes requires the presence of a free hydroxy group at C-3 and at least one free carboxylic acid in the molecular structure.

One or more of the acid triterpenes of the formula (I) can be formulated to a pharmaceutical composition together with any suitable excipient or adjuvant and applied to an oral cavity for the purpose of preventing dental caries. Such pharmaceutical composition for oral use may be in the form of a solid, liquid or semi-solid. Preferable compositions include tooth paste, gargle, troche, paint, cataplasma and chewing gum.

The carriers suitable for preparing the pharmaceutical composition, such as excipients and adjuvants, may be selected, depending on the type of the specific pharmaceutical composition, from those conventional to the art. Although not limited thereto, preferred carriers are lactose, starch, corn starch, magnesium stearate, carboxypolymethylene, hydroxypropylmethylcellulose (HPMC), calcium secondary phosphate ($2H_2O$), sorbitol, carboxymethylcellulose, saccharin, sodium laurylsulfate, glycerol, sodium carboxymethylcellulose, anhydrous Silicic acid, gelatin, titanium dioxide, menthol, fatty acids, citric acid, polyethyleneglycol, sodium lauroylsalcosinate, calcium carbonate, alcohol, carrageenan, sodium acyltaurate, pepton, acacia, lauryldiethanolamide, and the like.

Preservatives, perfumes, sweeting agents and dyestuffs can be added, if desired, to the pharmaceutical composition of the invention.

The content of the pentacyclic acid triterpene(s) of the formula (I) in the pharmaceutical composition of the invention varies depending on the type of particular composition. However, it is preferred to adjust the content of the triterpenes so that the concentration thereof may be more than about 0.001% (w/v), preferably more than 0.01% (w/v), at the locus where the pharmaceutical compositon is applied.

The following examples are presented by way of illustration of specific embodiments of the pharmaceutical composition of the invention, which contains pentacyclic acid triterpenes of the formula (I) as an essential component.

EXAMPLE 1

Tooth Paste

| Components | Weight (%) |
| --- | --- |
| Calcium secondary phosphate | 42 |
| Glycerol | 18 |
| Carrageenan | 1.0 |
| Sodium lauryl sulfate | 1.2 |
| Sodium oleate | 0.1 |
| Sodium glycyrrhetate | 0.05 |
| Butyl p-hydroxybenzoate | 0.03 |
| Flavor | 0.5 |
| $H_2O$ q.l. to make | 100.00 |

According to any one of the conventional methods, tooth paste is prepared using the above components. Water, glycerol, carrageenan, sodium oleate, sodium glycyrrhetate, butyl p-hydroxybenzoate and perfume are each weighed and admixed all together, whereby the carrageenan is swollen. To the resulting mixture are added calcium secondary phosphate and sodium lauryl sulfate, and all the components are thoroughly blended. The resultant mixture is filled in a tube after deaeration.

EXAMPLE 2

Mouth-Wash

| Component | Weight (%) |
| --- | --- |
| Ethanol | 20.0 |
| Sodium ursolate | 1.0 |
| Sodium glycyrrhetate | 0.5 |
| Sodium acyltaurate | 0.5 |
| Sodium methylcellulose | 0.5 |
| Gelatin | 0.5 |
| Flavor | 0.5 |
| $H_2O$ q.l. to make | 100.0 |

The above components are dissolved in a mixture of $H_2O$ and ethanol to obtain a mouth-wash concentrate. This concentrate is used after diluted to 1/50–1/100.

EXAMPLE 3

Troche

| Component | Weight (%) |
| --- | --- |
| Acacia | 8.0 |
| Lactose | 88.5 |
| Oleanolic acid | 0.3 |
| Glycyrrhetic acid | 0.2 |
| Flavor | 1.0 |
| Magnesium stearate | q.l. |

Acacia, lactose, oleanolic acid and glycyrrhetic acid are weighed and thoroughly admixed. To the mixture is added a suitable amount of water, and the resulting mass is granulated using a conventional granulator and dried. The obtained granule is passed through 12 mesh screen and combined with the perfume and magnesium stearate. The resulting mixture is compressed by means of a conventional compressor to obtain a troche.

EXAMPLE 4

| Component | Weight (%) |
| --- | --- |
| Gum Base | 20.0 |
| Oleanolic acid | 0.1 |
| Pomolic acid | 0.1 |
| Saccharin | 0.05 |
| Lactose | 64.05 |
| Maltose | 10.90 |
| Flavor | 1.0 |
| Calcium carbonate | 3.0 |
| | 100.0 |

Chewing Gum

Chewing gum composition is prepared in a conventional manner using the above components.

EXAMPLE 5

Tooth Powder

| Component | Weight (%) |
|---|---|
| Calcium secondary phosphate(2H$_2$O) | 50.0 |
| Calcium carbonate | 30.0 |
| Glycerol | 10.0 |
| Sodium lauryl sulfate | 1.3 |
| Glycyrrhetic acid | 0.1 |
| Hederagenine | 0.1 |
| Flavor | 1.0 |
| Carboxymethylcellulose | 5.0 |
| H$_2$O q.l. to make | 100.0 |

In accordance with a conventional procedure, a tooth powder is prepared using above components.

What is claimed is:

1. A pharmaceutical composition for the prevention of dental caries which comprises an anti-caries effective amount of one or more pentacyclic acid triterpene of the formula

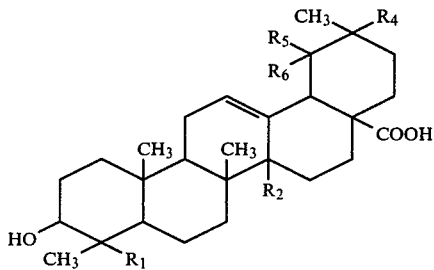

wherein $R_1$ is CH$_3$, CHO or CH$_2$OH,
$R_2$ is CH$_3$ or COOH,
$R_4$ is H, CH$_3$ or COOCH$_3$,
$R_5$ is H, CH$_3$ or OH, and
$R_6$ is H, CH$_3$ or OH and pharmaceutically acceptable salts thereof and a pharmaceutically acceptable carrier.

2. The pharmaceutical composition of claim 1 wherein said pentacyclic acid triterpene are selected from the group consisting of oleanic acid, ursolic acid, pomolic acid, quinovic acid, hederagenin, spergulagenic acid, gypsogenin, and phytolaccinic acid.

3. The pharmaceutical composition of claim 1 wherein said pentacyclic acid triterpene are selected from the group consisting of oleanolic acid, ursolic acid, pomolic acid, and hederagenin.

4. The pharmaceutical composition of claim 1 wherein said pentacyclic acid triterpene are selected from the group consisting of oleanic acid, ursolic acid and hederagenin.

5. A method for preventing dental caries which comprises applying to an oral cavity the composition of claim 1.

6. The method of claim 5 wherein said pentacyclic acid triterpene are selected from the group consisting of oleanolic acid, ursolic acid, pomolic acid, quinovic acid, hederagenin, spergulagenic acid, gypsogenin, and phytolaccinic acid.

7. The method of claim 5 wherein said pentacyclic acid triterpene are selected from the group consisting of oleanolic acid, ursolic acid, pomolic acid, and hederagenin.

8. The method of claim 5 wherein said pentacyclic acid triterpene are selected from the group consisting of oleanolic acid, ursolic acid and hederagenin.

* * * * *